United States Patent [19]

Grube et al.

[11] 4,399,367

[45] Aug. 16, 1983

[54] PROCESS AND APPARATUS FOR DETECTING AND SORTING OUT INAPPROPRIATELY FILLED PACKAGES OF FILLER MATERIAL DURING A PACKAGING PROCESS

[75] Inventors: Gerhard Grube; Heinz Engelke, both of Loehne, Fed. Rep. of Germany

[73] Assignee: Otto Haensel GmbH, Hanover, Fed. Rep. of Germany

[21] Appl. No.: 182,660

[22] Filed: Aug. 29, 1980

[30] Foreign Application Priority Data

Aug. 31, 1979 [DE] Fed. Rep. of Germany ....... 2935153
Aug. 31, 1979 [DE] Fed. Rep. of Germany ....... 2935154

[51] Int. Cl.³ ............................................. G01N 21/86
[52] U.S. Cl. ................................. 250/560; 250/223 R; 356/379
[58] Field of Search ........................ 209/576, 586, 588; 250/560, 561, 223 R, 223 B, 562, 572; 356/379, 380, 384–387, 394

[56] References Cited

U.S. PATENT DOCUMENTS

| | | | |
|---|---|---|---|
| 2,179,000 | 11/1939 | Tea | 356/379 |
| 2,627,347 | 2/1953 | Powers | 209/586 |
| 3,521,749 | 7/1970 | Dijstelbergen et al. | 356/380 |
| 3,882,316 | 5/1975 | Garris | 250/560 |

Primary Examiner—David C. Nelms
Attorney, Agent, or Firm—Watson, Cole, Grindle & Watson

[57] ABSTRACT

Packages include a bottom foil having spaced nests formed therein and a cover foil. At least the bottom foil is permeable to radiation so that it may be irradiated on one side with a source of radiation following a filling station during movement of the packages through a packaging machine. The intensity of the radiation allowed to pass through the bottom foil is measured by a radiation receiver having an active receiving surface which overlies the filler material and which surface is greater than the surface of the filler material facing it. The radiation through the bottom foil casts filled nests onto the receiving surface. The shadow of a nest inappropriately filled differs from a shadow of the nests appropriately filled with the filler material. An apparatus is triggered for sorting out an inappropriately filled nest by starting signals of a receiver whenever the amplitude thereof fails to reach a predetermined value. The bottom foil may otherwise be of a material capable of reflecting incident radiation so as to be irradiated with a source of rays with reflected radiation being measured by the radiation receiver.

12 Claims, 11 Drawing Figures

Fig.1
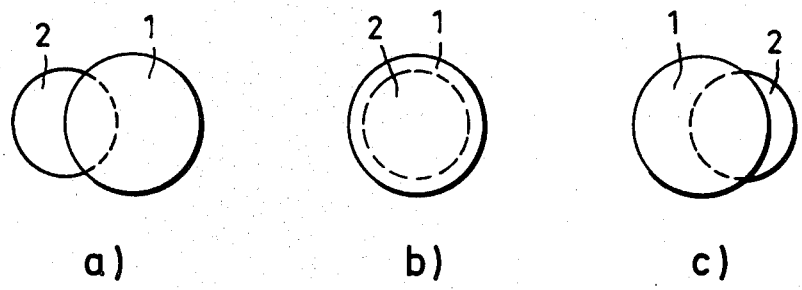
a)   b)   c)
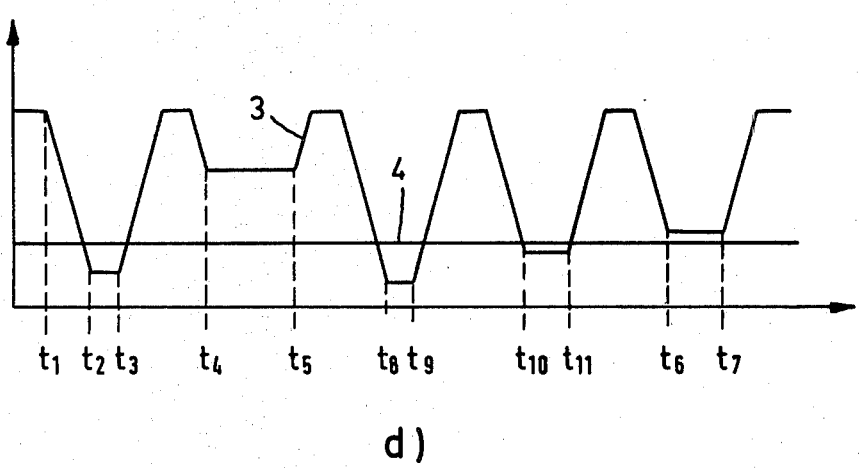
$t_1$ $t_2$ $t_3$   $t_4$   $t_5$   $t_8$ $t_9$   $t_{10}$ $t_{11}$   $t_6$ $t_7$
d)
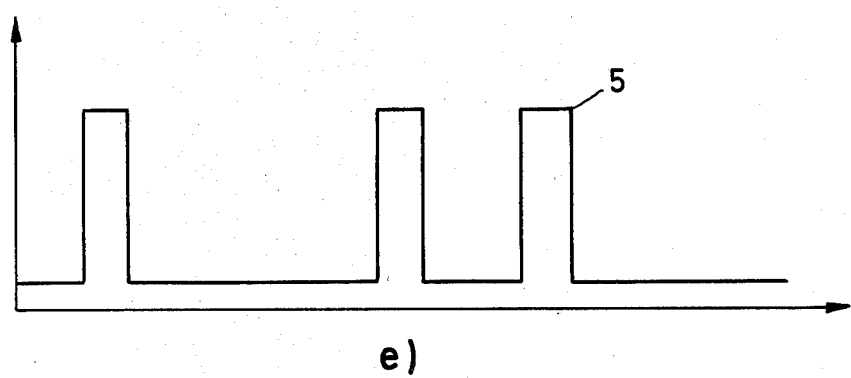
e)

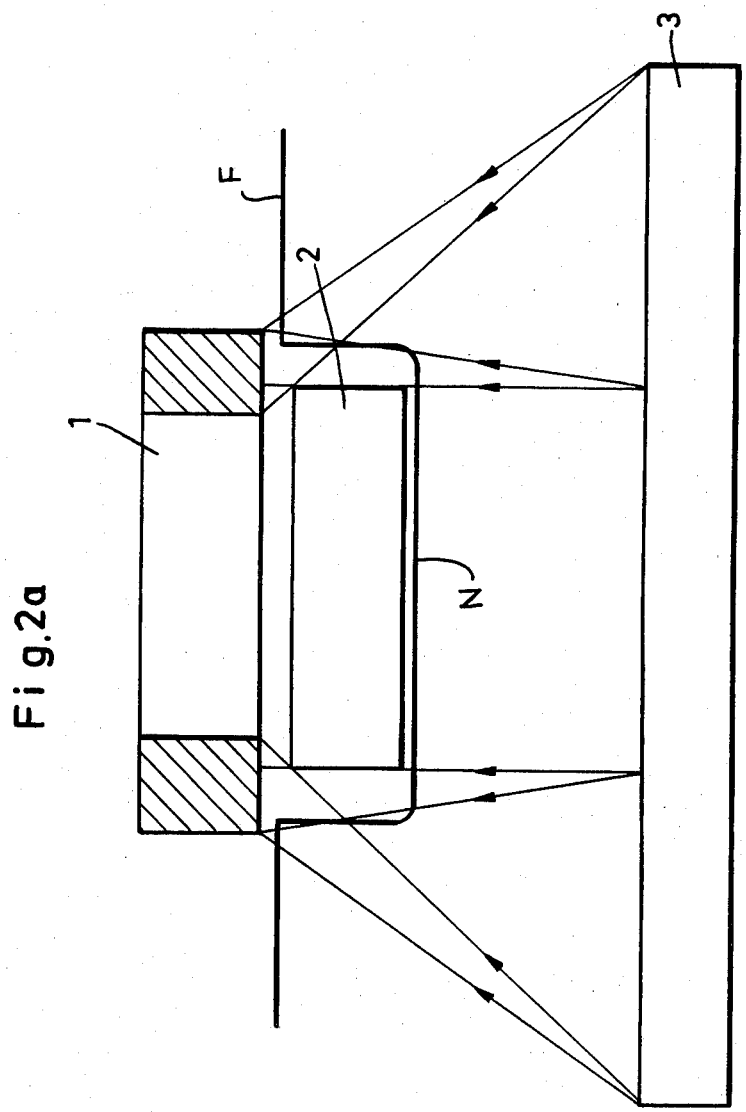

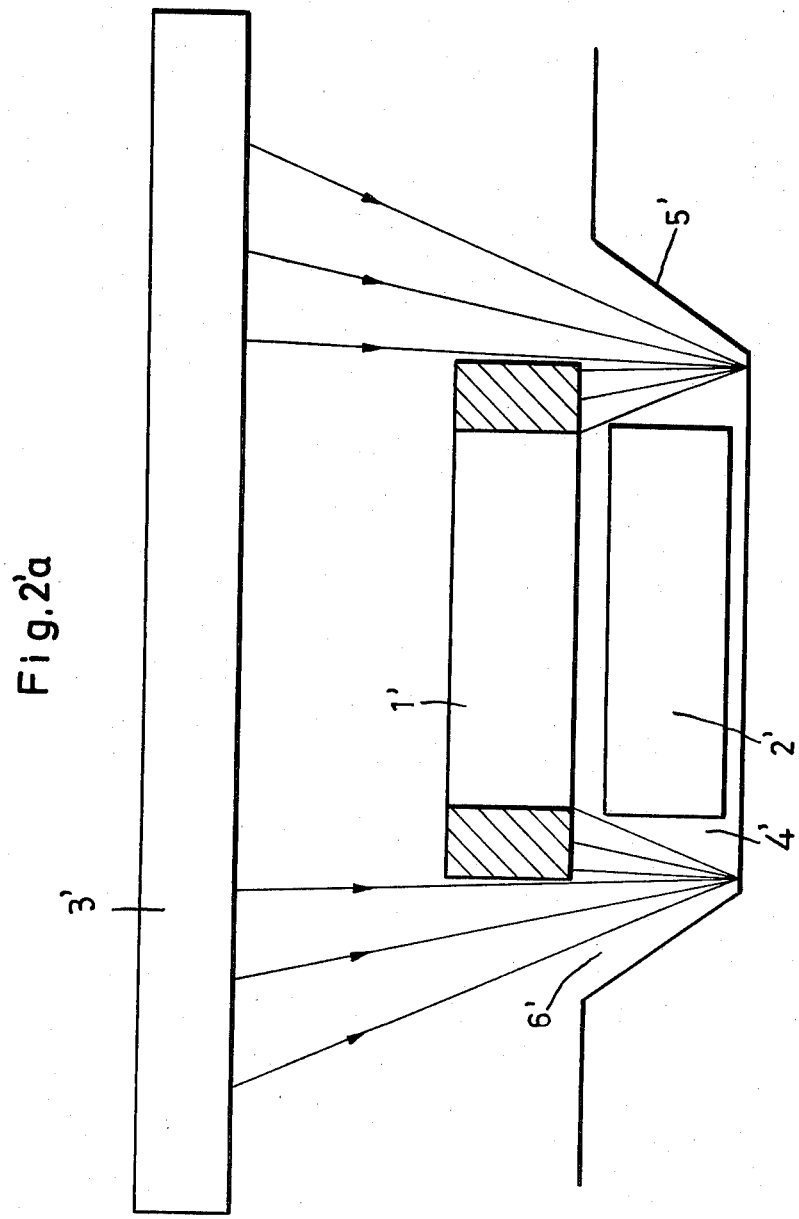

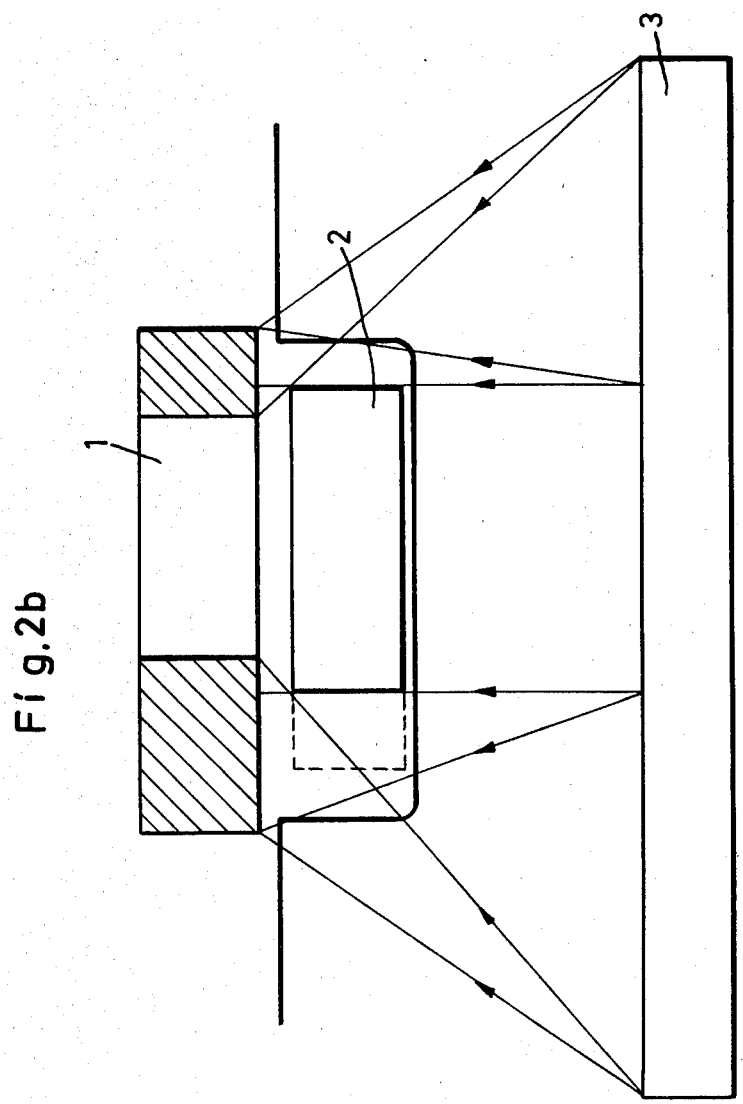

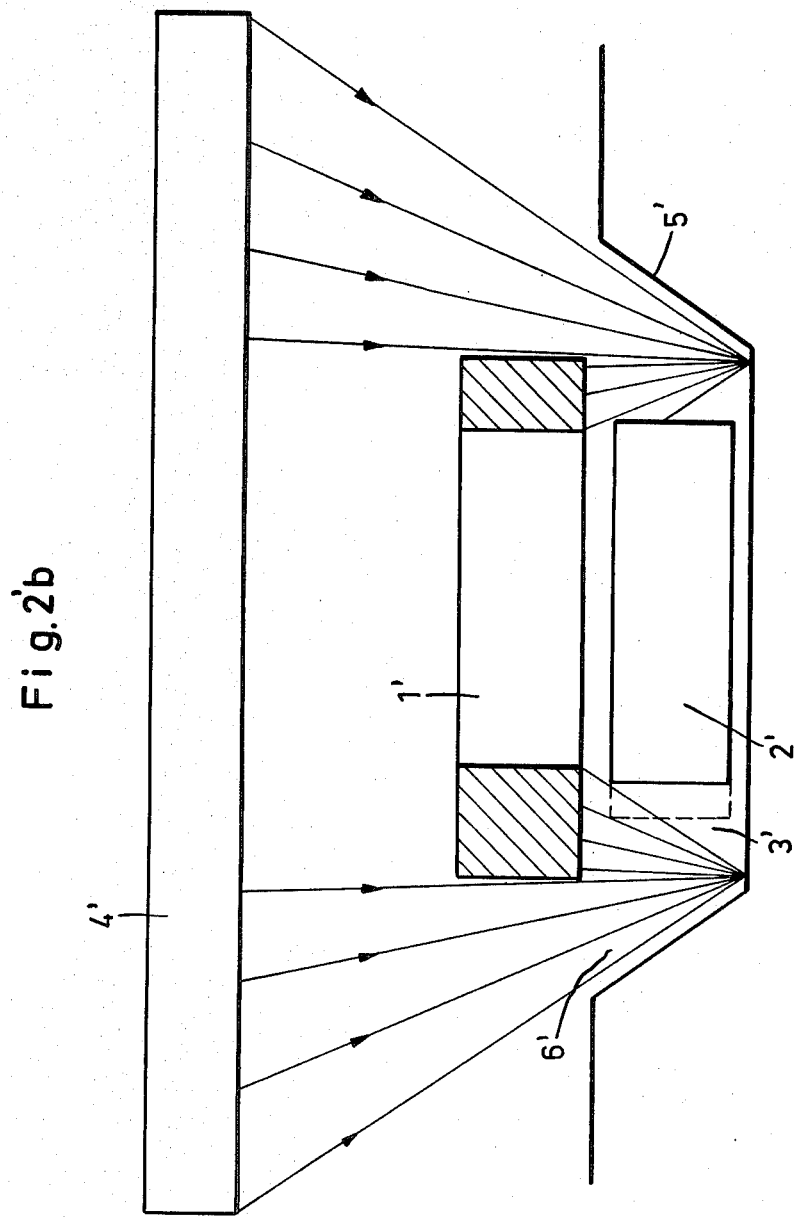

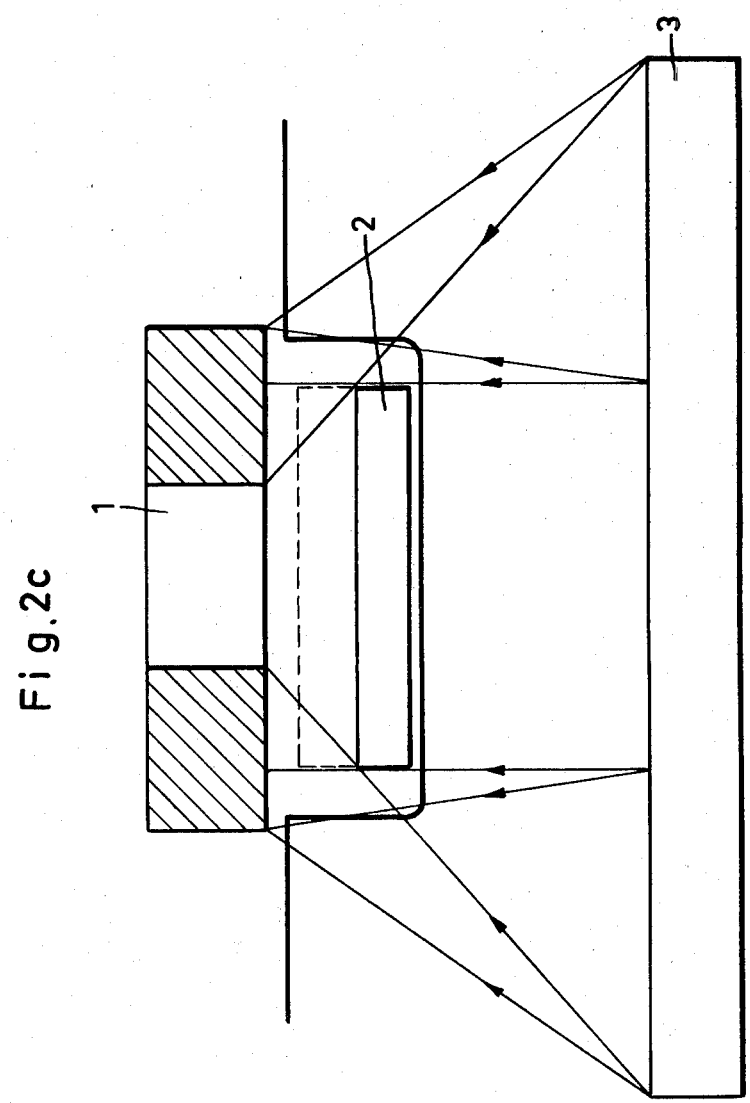

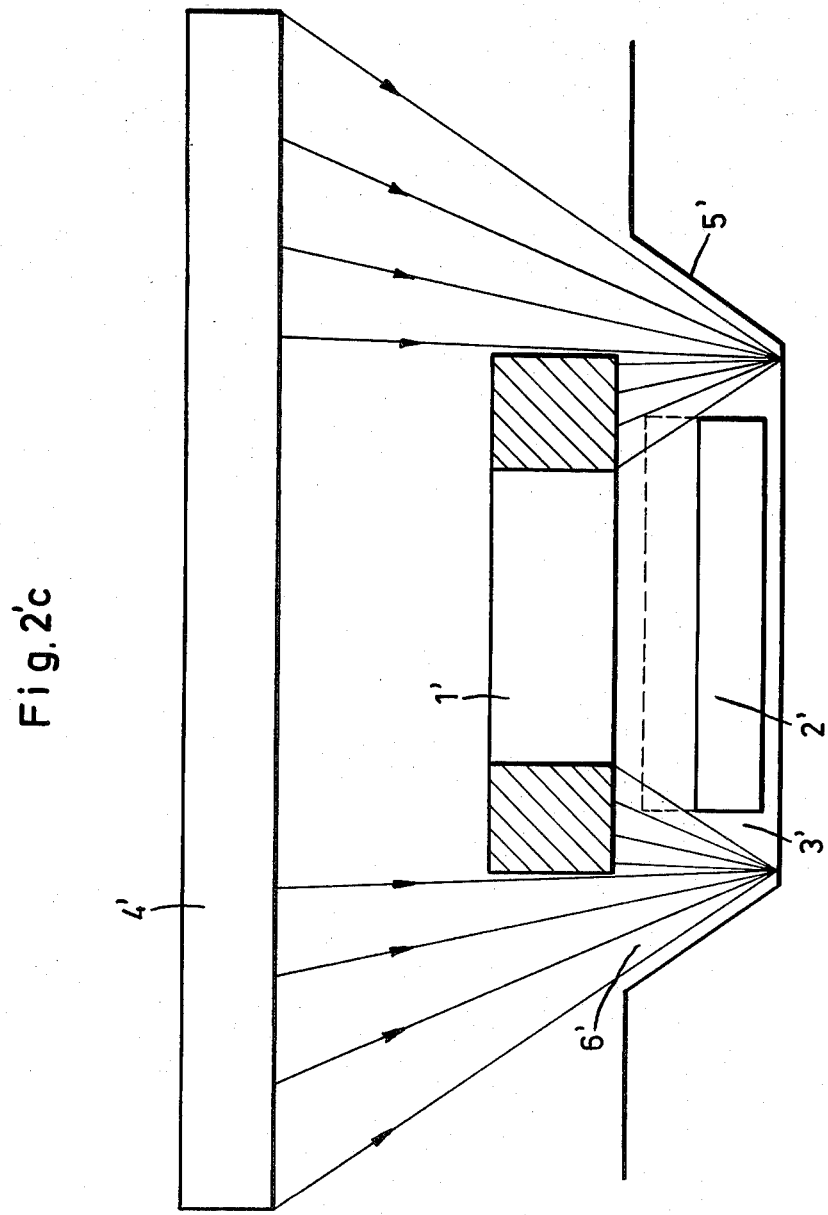

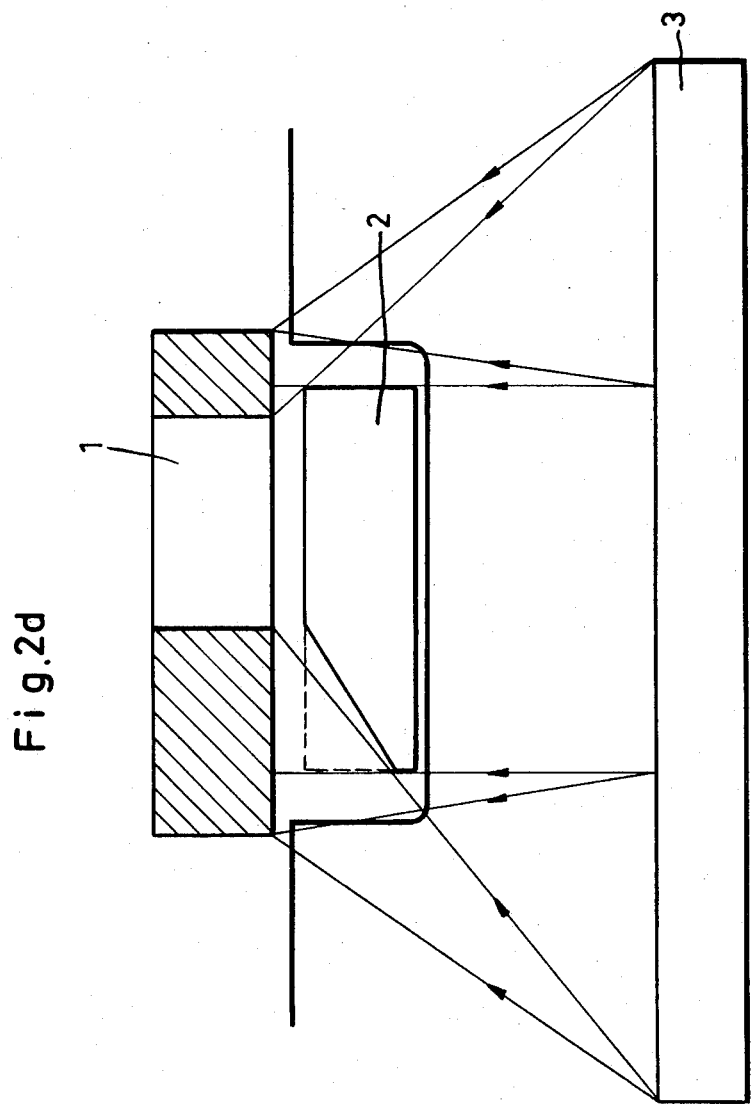

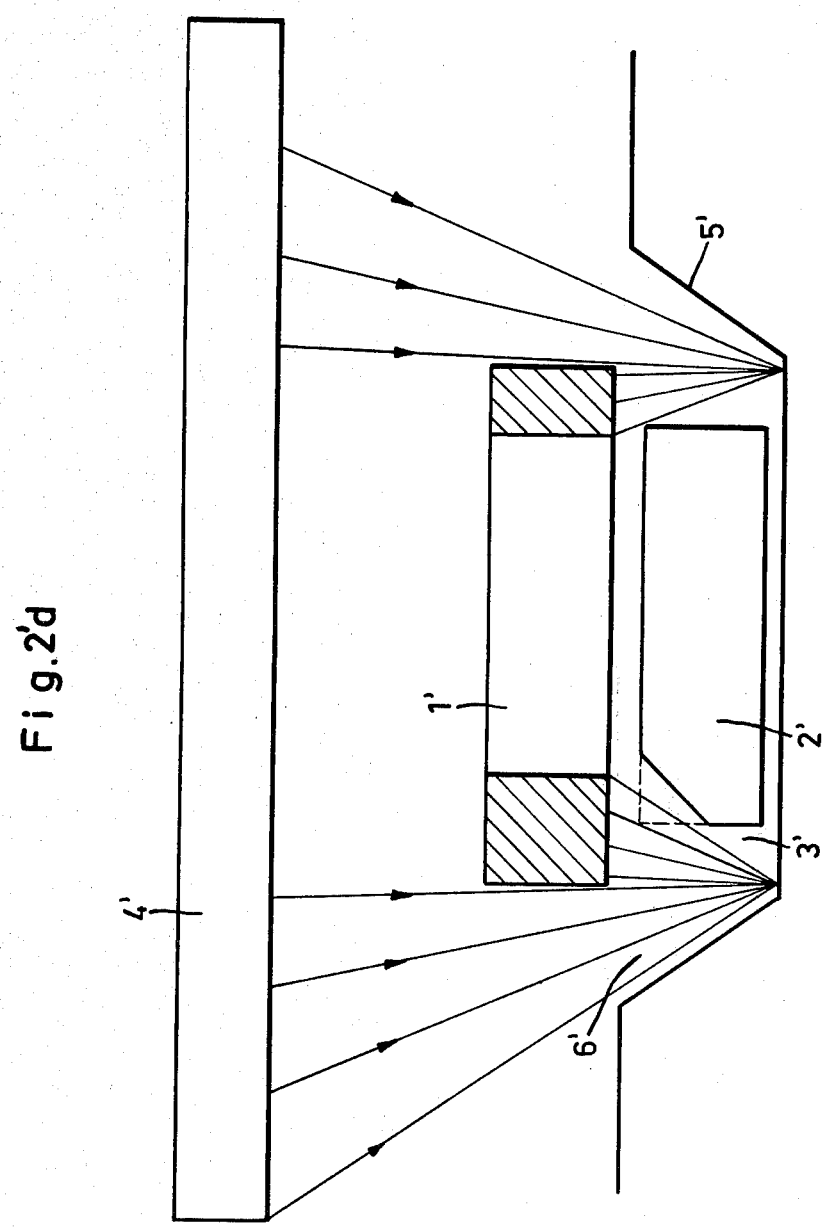
Fig.2'd

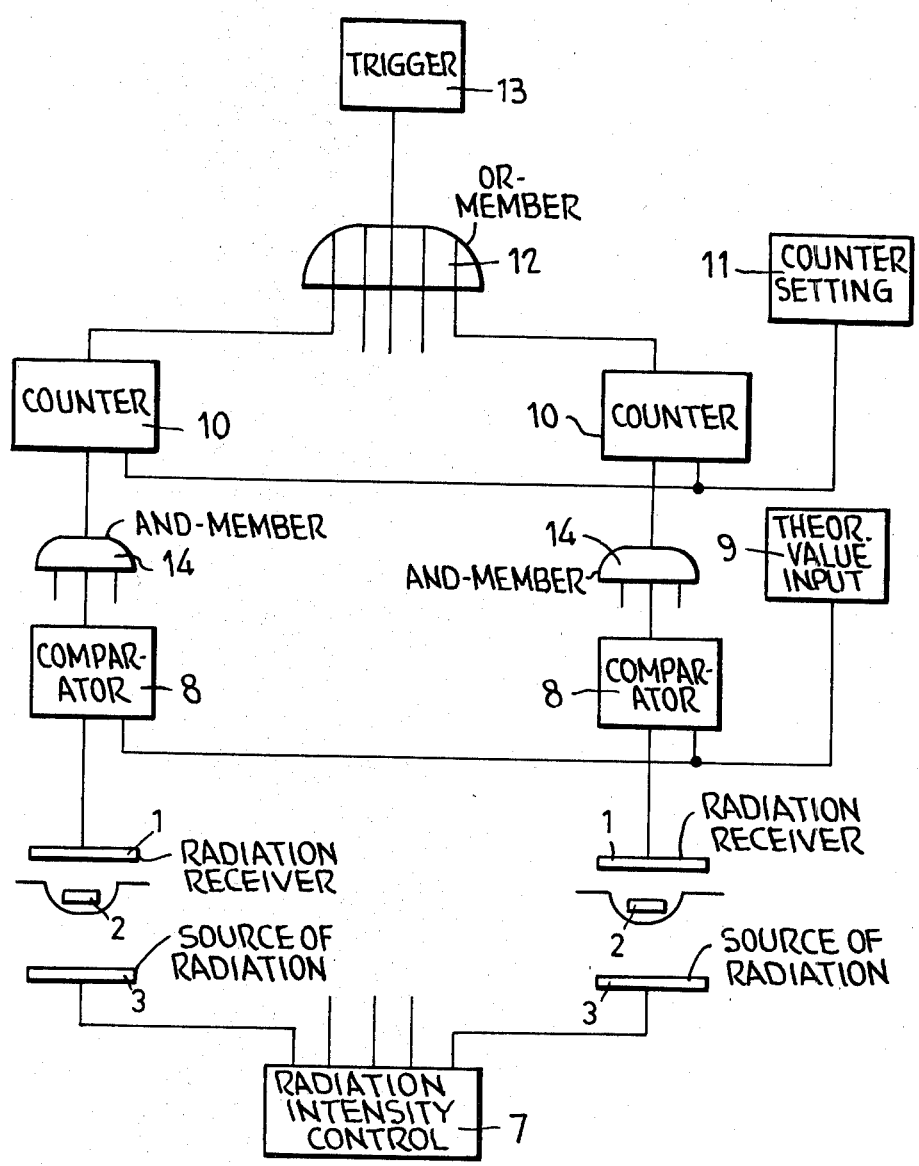

PROCESS AND APPARATUS FOR DETECTING AND SORTING OUT INAPPROPRIATELY FILLED PACKAGES OF FILLER MATERIAL DURING A PACKAGING PROCESS

BACKGROUND OF THE INVENTION

1. Field of the Invention

This invention relates generally to a process and apparatus for detecting and sorting out inappropriately filled packages of filler material during a packaging process, each package comprising a bottom foil having spaced nests formed therein and a cover foil, and at least the bottom foil being permeable to radiation so that when irradiated on one side thereof with a source of radiation the intensity of the radiation allowed to pass through the bottom foil is measured by at least one radiation receiver. The bottom foil may be otherwise of a material capable of reflecting incident radiation so that when irradiated with a source of rays the reflected radiation is measured by the radiation receiver.

It is to be understood that a radiation permeable foil is one through which rays may pass. The foil may thus comprise a light permeable foil material, whenever the source of rays is a source of light. The receiver may correspondingly comprise a photo element. And, the source of radiation may comprise an infrared radiator so that a non-transparent foil material will be selected. Whenever the bottom foil only is permeable to rays, the detection of inappropriately filled packages is carried out prior to the sealing of the package nests with the cover foil. However, if both bottom and cover foils are permeable to radiation, then such detection may be carried out after the cover foil is sealed in place.

And, it is to be understood that when the foil is described as capable of reflecting incident radiation, it may be of a material capable of reflecting visible light whenever the source of radiation comprises a light source. A photo element would thus be selected as the receiver. The transmitter or source of radiation may alternatively comprise an infrared radiator.

2. Description of the Prior Art

In the production of deep-dished packages for filler material, the bottom foil is normally drawn off a supply roll and is fed through deflecting rolls during the packaging process for forming a plurality of nests. The bottom foil having the nests formed therein are then guided through the filling station and are filled with the selected filling material which may comprise pills, tablets, or the like, after which the cover foil is welded or otherwise secured in place. The nests of the package are generally disposed in rows both parallel to and perpendicular to the direction of movement of the packages through the packaging machine. The cover foil overlies several mutually perpendicular rows of spaced nests, and the covered packages are fed to a stamping station at which they are stamped and cut into packages of predetermined numbers of spaced nests. And, those subdivided packages having one or more nests thereof inappropriately filled with the filler material are sorted out in some manner by rejecting them as not meeting the necessary quality control standards.

In order to detect inappropriately filled packages, it has been known to provide mechanical arrangements disposed between the filling station and the sealing station above the bottom foil. By such arrangements, pegs, levers, or roller levers are lowered into the nests and a signal is obtained upon direct contact with the filler material or with the nest to determine whether the nest is appropriately filled. And, the pegs or levers are normally combined into groups capable of use with only a predetermined array of nests for a particular package.

Moreover, German Pat. No. 26 31 138 discloses an apparatus for detecting and sorting out faulty packages which are made during a packaging process. A video picture is taken of a package free of faults and is stored electronically, and succeeding video pictures of the package nests filled with the particular filler material are then compared against this stored video picture. A video camera located behind the filling station photographs ranges of the bottom foil always representing a group of packages predetermined according to length and width. Thus, an arrangement is developed such that filled nests of a package group in the photographed area imbued with faults or without faults determined by comparison are recognized, and the inappropriately filled packages of a pertinent group of packages are sorted out after a stamping operation.

It has also been known to carry out a detecting and sorting out process by a transmitted light technique, whereby a light transmitter is disposed on one side of the bottom foil with a light receiver on the other side. Interruption of the ray of light is therefore indicative of whether or not the nests are filled, the filler material providing an opto-electronic barrier.

Further, in the present area to which the present invention relates, it is known to dispose a transmitter and a receiver in such a matter that the reflected light is picked up by the receiver. Thus, whenever a nest of the package is empty the intensity of the light is insufficient to actuate response by the receiver. Only when the path of the light rays is shortened by a filler material located in the nest will the receiver respond, since the filler material acts as an opto-electronic barrier. However, it is not possible with these known techniques to determine whether or not the filler material has the prescribed size but only whether the particular are filled or not. It has therefore not been possible to sort out packages containing faulty filler material contained within one of the package nests.

SUMMARY OF THE INVENTION

It is an object of the present invention to provide a process and apparatus for detecting and sorting out not only packages having a nest or nests thereof empty of the intended filler material, but also capable of detecting and sorting out inappropriately filled packages of filler material such as those which are faulty or damaged, for example, broken tablets, pills, or the like. The bottom foil forming the package is irradiated on one side by a source of radiation as the package proceeds through the packaging machine. The irradiating station is disposed behind the filling station and the shadow of the filled nest onto the receiving surface generates a signal which indicates if the nest is filled or not.

Another object of this invention is to provide such a processing apparatus wherein the active receiving surface of the receiver overlies the filler material and is greater than the surface of the filler material facing it. The output signals of the receiver triggers an apparatus for sorting out the inappropriately filled nest whenever the amplitude of those signals fails to reach a predetermined value. Rays from the radiation source pass through the bottom foil and cast a shadow of the nest onto the receiving surface when the nest being irradiated is appropriately filled with the filler material. However, when the irradiated nest is inappropriately filled with the filler material, the area of the shadow cast on the receiving surface differs from the area of the shadow cast when irradiating the nest appropriately filled with the filler material. As a result, the amplitude of the starting signal of the receiver decreases in accordance with the decrease in irradiated surface area. This starting signal decreases until the tablet has moved during the packaging process completely into the field of vision of the receiver, and it remains constant until the tablet begins to move out of such field of vision. Consequently, a signal is generated at the outlet of the receiver, the amplitude or level of impulse of which is determined by the ratio of irradiated receiving surface before and after the tablet moves into the field of vision of the receiver. Basically, a parallel bundle of light could be directed toward the receiver. Consequently, the mere breakage of the tablet is capable of being detected for a break running perpendicularly to the diameter of the tablet. For this reason, diffusely emitted rays are used so that even some other tablet breakage can be detected. In accordance with the present invention, only perfect filler material within the package nest being irradiated will be capable of lowering the amplitude of the starting signal on the receiver below a predetermined value which requires no sorting out of the particular package. Thus, the present process and apparatus assures that not only packages with empty nests, but also packages containing faulty filler material can be detected and sorted out.

In accordance with another object of the invention, at least the bottom foil forming the package may be alternatively of a material capable of reflecting incident radiation, so that the reflected radiation is measured by the receiver in such a manner that both empty package nests as well as nests containing damaged or inappropriately filled filler material can be detected and sorted out. The shadow casting onto the receiving surface of the receiver is similar to that described above, and a tablet or the like moves into the field of vision of the receiver, its active receiving surface is partially covered up. As a result, the irradiated surface is reduced and the amplitude of the starting signals of the receiver also decreases. The starting signal decreases until the tablet has moved completely into the field of vision of the receiver and it remains constant until the tablet again moves out of such field of vision. Consequently, a signal is delivered at the outlet of the receiver, the amplitude or level of impulse of which is determined by the ratio of the irradiated receiving surface prior to and after movement of the tablet into the field of vision of the receiver.

It is essential that diffusely emitted rays be used in carrying out the invention so as to assure that only filler material free of faults will be in a position to lower the amplitude of the starting signal at the receiver to a minimum. As a result, it is assured by the invention that not only packages with empty nests are capable of being detected but also packages containing faulty filler material can be detected and sorted out.

The apparatus according to the invention functions equally as well for both continued as well as timed movement of the bottom foil during the packaging process, the spaced nests formed in the foil in rows and the radiation receiver being provided for each row of nests moving into and out of vision of that receiver in the direction of foil movement through the packaging machine. Comparators are connected with the receivers on the outlet side thereof always with a second inlet for a comparative signal, and counters are connected with the receivers at the outlet side for counting the number of nests in a particular row. An arrangement is connected to the comparators and to the outlet sides of the counters for triggering an apparatus for sorting out inappropriately filled nests when the amplitude of the output signals of the receiver fail to reach a predetermined value.

Only whenever filler material free of faults is located in a nest being irradiated, impulses to the counters connected on the outlet side are delivered by the comparators via an AND-member. The counters for a particular row are connected by an OR-member. After all the nests of the package are moved past the receiver, the counter condition is noted. Whenever a prescribed final condition has not been reached, the device connected at the outlet side for sorting out the package is triggered by way of the OR-member.

According to a further embodiment of the invention, the apparatus is characterized by the provision of one receiver for each nest of a package, by comparators connected on the outlet side to the receiver with one inlet for a comparative signal, as well as by an arrangement connected to the comparators on the outlet side for sorting out an appropriately filled package when the amplitude of the output signals of the receivers, associated with the nests being irradiated, fails to reach the predetermined value. As a result, the receivers are disposed in a matrix corresponding to the configuration of the nests. The outlets of the comparators assigned to the receivers are joined by an AND-member. The counters may thus be eliminated.

In both embodiments the apparatus operates in such a manner that starting signals of the receivers are delivered to the additional circuit components only if the package being tested has assumed the proper position beneath the receivers. The switching expenditure is, however, considerably greater since the receiver with a comparator must be provided for each nest, although the counters are omitted. Such apparatus may be used especially for packages having the same or similar formats to be produced.

BRIEF DESCRIPTION OF THE DRAWINGS

FIGS. 1a, 1b, 1c, 1d and 1e diagrammatically illustrate the basic principle in carrying out the invention;

FIGS. 2a, 2b, 2c, and 2d diagrammatically illustrate an emitter, a receiver, and a tablet detected in a package nest in accordance with one embodiment of the invention;

FIGS. 2'a, 2'b, 2'c, and 2'd illustrate another embodiment of the invention similar to the above;

FIG. 3 is a diagrammatic illustration of an apparatus for carrying out the process of the invention according to a counting principle.

DETAILED DESCRIPTION OF THE PREFERRED EMBODIMENT

Figure 4:
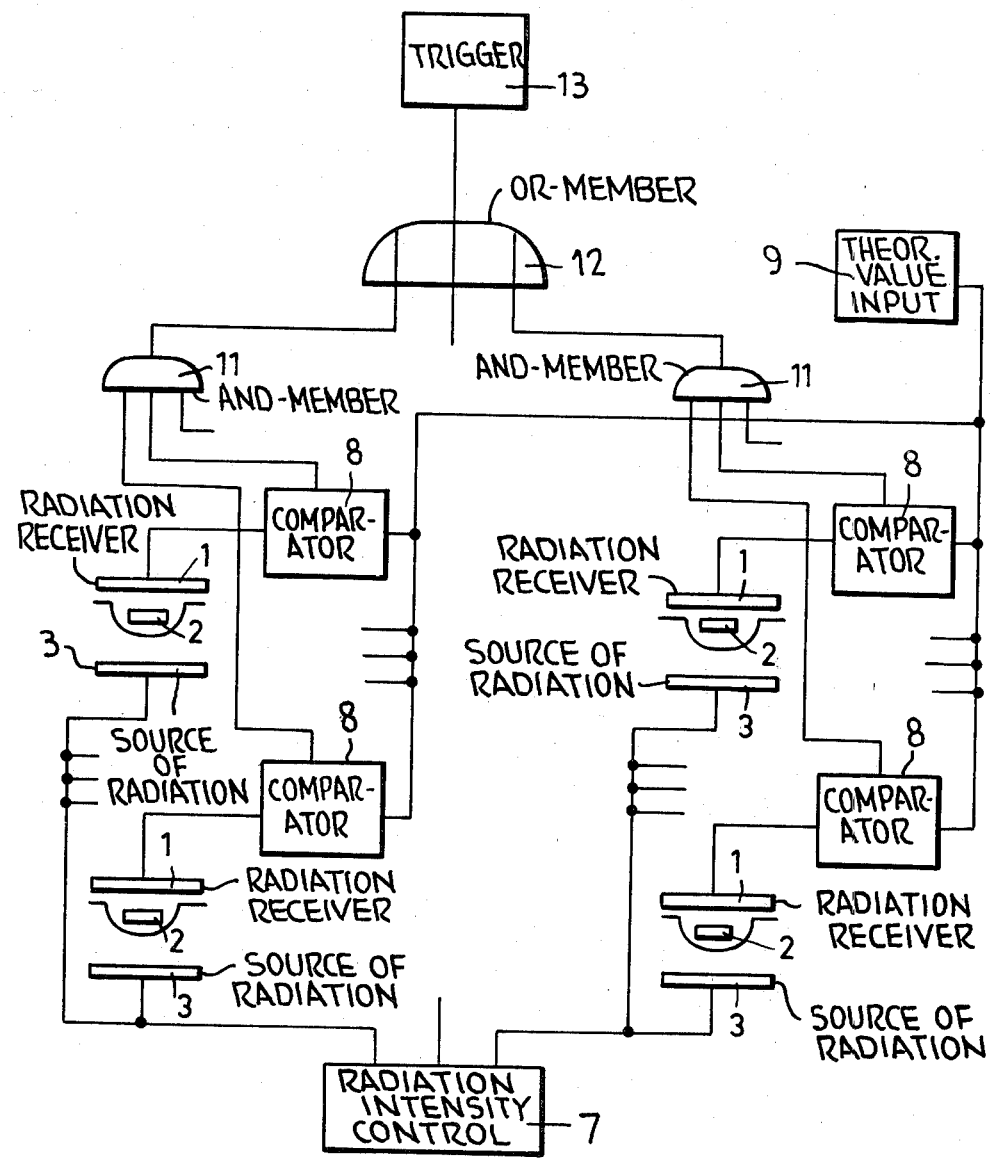
FIG. 4 is a diagrammatic illustration of an apparatus for carrying out the process of the invention wherein detection of a package is made by using one receiver for each nest.

Turning now to the drawings wherein like reference characters refer to like and corresponding parts throughout the several views, the active surface of a radiation receiver is generally designated 1 in FIGS. 1a, 1b, and 1c, and the surface of a tablet is shown at 2 the shadow of which, during movement of the bottom foil through the packaging machines, passes through the field of vision of the receiver. In FIG. 1b, the received volume of radiation is shown as an analogous electrical signal, the starting signal being designated 3 and the theoretical voltage (threshold value) being designated 4, while FIG. 1e shows the associated digital presentation designated by reference reference numeral 5. As long as the tablet remains outside the field vision of the receiver a constant starting signal is delivered by the receiver. Thus, at a time $t_1$, the tablet moves into the field of vision of the receiver (FIG. 1a) and as a result a portion of the active receiving surface is covered up. As a consequence, the radiation volume decrease is through a time interval $t_2$ when the tablet is located completely within the confines of the active receiving surface of the receiver (FIG. 1b).

At a time $t_3$ the tablet moves out of the field of vision of the receiver (FIG. 1c), so that the irradiated active receiving surface again becomes greater, i.e., the received radiation volume (energy per time) increases until the starting signal reaches its original constant volume prior to time $t_1$, i.e., when the appropriately filled nest has left the field of vision of the receiver. Whenever the nest is filled with only half the tablet, then a receiving surface which is greater by one-half than that of an undamaged tablet is irradiated, so that the amplitude of the signal is smaller. Whenever the nest being detected is empty, then a corresponding signal is missing, i.e., the receiving element records at the outlet the unchanged voltage prior to the time of $t_1$.

For various types of damaged tablets, the amplitudes are shown in time intervals $t_4$–$t_5$, $t_6$–$t_7$, the amplitudes at time intervals $t_2$–$t_3$, $t_8$–$t_9$, and $t_{10}$–$t_{11}$ evidencing tablets the size of which exceed the minimum size. By the comparison of these voltages with the theoretical voltage (threshold voltage), it may be unequivically determined whether there is a breakage of the tablet or whether the nest is filled. FIG. 1e shows the comparative results in digital presentation. Here, in time intervals $t_4$–$t_5$ and $t_6$–$t_7$, no impulses are obtained. Whenever the presentation in FIG. 1d corresponds to a package having five nests which are detected, it can be clearly seen that breakages are detected for two of the tablets since only three impulses are assigned to the package. Thus, an arrangement for sorting out the package is triggered by a corresponding circuit arrangement to be more fully explained hereinafter.

FIGS. 2a, 2b, 2c, and 2d generally illustrate the inventin in carrying out the principle process. These Figures illustrate the same principle according to the invention as in FIG. 1, except that the emitter, receiver and tablet are shown in side elevation rather than in plan view as in (FIG. 1b). In FIG. 2a, radiation receiver 1 can be seen as having an active receiving surface which overlies tablet 2 and which surface is greater than the surface of this filler material facing it. The tablet is contained in a nest N of a bottom foil F which moves relative to the stationary receiver during the packaging process. The tablet is irradiated with rays from a source of rays or emitter 3, and casts a shadow upon an area of the receiving surface (shown by the unhatched portion of receiver 1). Thus, for an undamaged tablet or other type filler material, as in FIG. 2a, a maximum shadow area (unhatched) of the receiver is shadowed.

The tablet in FIG. 2b is shown ruptured vertically so that emitted rays will cast a shadow (shown unhatched) onto a correspondingly smaller area of the receiver. In FIG. 2c a ruptured tablet is shown having only about one-half its intended thickness. A smaller surface is likewise covered up as compared to that covered up in FIG. 2a. And, another type of ruptured tablet is shown in FIG. 2d, and a corresponding decreased area of the active receiving surface is shown and compared against that of FIG. 2a.

Therefore, in the FIG. 2 embodiment wherein the bottom foil is permeable to radiation, different types of faulty filler material can be detected as a parallel bundle of light is directed perpendicularly onto the bottom foil and thus onto the tablets.

Another principle used in carrying out the invention is illustrated in FIGS. $2'a$, $2'b$, $2'c$, and $2'd$. Again, these Figures constitute schematic side elevations of a radiation emitter, a radiation receiver, and tablet contained within the nest of a bottom foil moving relative to the emitter and receiver. FIG. 1b by comparison, constitutes a top plan view. At the filling station of the packaging apparatus, a nest $4'$ of the bottom foil is shown in FIG. $2'a$ as having been filled with a tablet $2'$. The active receiving surface of a radiation receiver $1'$ overlies the tablet and has a surface greater than the surface of the tablet surface facing it. An emitter or source of radiation $3'$ overlies the receiver. The tablet has a smaller diameter than its nest so as to define an annular gap $6'$ with a side wall $5'$ of the nest. The bottom foil is of a material capable of reflecting incident radiation, so that diffusely emitted rays entering annular gap $6'$ are reflected. Thus, for an undamaged tablet shown in FIG. $2'a$, a shadow (shown unhatched) is cast by the reflected rays onto the receiving surface and having a maximum area. A shadow cast by the reflecting rays when detecting a damaged tablet having a vertical rupture as in FIG. $2'b$, on the other hand is smaller (unhatched section of the receiver) as compared to that of the un-hatched section of the receiver of FIG. $2'a$. Likewise, for the damaged tablets shown in FIGS. $2'c$ and $2'd$—the shadows cast onto the receiver surface are correspondingly smaller than that of FIG. $2'a$ for an undamaged tablet.

FIG. 3 is a block diagram of an apparatus for carrying out the process of the invention, wherein one receiving element 1 is provided for each row of nests moving in the direction of the bottom foil during the packaging process. The tablets 2 are irradiated through the bottom foil by a source 3 of rays, similarly as described with reference to FIG. 2. However, the principle described with reference to FIG. $2'$ can likewise be incorporated into the FIG. 3 apparatus without departing from the spirit of the invention.

Thus, the apparatus according to FIG. 3 is capable of detecting inappropriately filled packages of filler material along a pair of rows of nests formed in the bottom foil. The radiation intensity is predetermined jointly for both sources of radiation by means of a control member 7. The starting signals of the receivers are fed to their assigned comparators 8 and are compared with a reference voltage provided by a theoretical value input device 9. The comparative result is transformed into the digital presentation shown in FIG. 1e, and the impulse delivered by the outlet of the comparators are fed through associated counters 10 via an AND-member 14, the counters being associated with the respective rows of nests being detected. The counters substract the number of incoming impulses from its meter reader. After the passage of a package equals zero as shown by the meter reader, that passage is appropriately filled (such as undamaged tablet). The setting of the counters is accomplished by a device 11.

However, whenever a nest is empty or is inappropriately filled, then the assigned counters will show a meter reading different from zero. Accordingly, an impulse reaches an arrangement 13 by way of an OR-member 12 connected at the outlet side to each of the counters, such arrangement being provided for triggering an apparatus (not shown) for sorting out the package having an inappropriately filled nest of filler material.

FIG. 4 is a block diagram of another apparatus for carrying out the invention without the use of counters or a counter setting device or a theoretical counter input device. Here, a receiver is associated with each nest of the package, a comparator being connected at the outlet side of each receiver with one inlet for a comparative signal, and an arrangement 13 being connected to the comparators at the outlet side for sorting out the particular package, similarly as described with reference to FIG. 3. Thus, the receivers are disposed in a matrix corresponding to the configuration of the nests formed in the bottom foil. The outlets of the comparators assigned to the receivers are joined by an AND-member.

Obviously, many modifications and variations of the present invention are made possible in the light of the above teachings. It is therefore to be understood that within the scope of the appended claims the invention may be practiced otherwise than as specifically described.

What is claimed is:

1. A process using a radiation source, a radiation receiver and a sorting apparatus for detecting and sorting out packages of filler material inappropriately filled during movement of said packages through a packaging machine wherein each of said packages comprises a cover foil and a radiation permeable bottom foil having a plurality of spaced nests formed therein for holding said filler material such that each of said nests is dimensioned to form a gap around said filler material after filling of said nests and wherein said process comprises:
    providing said radiation receiver with an active receiving surface overlying an adjacent surface portion of said filler material such that said receiving surface is larger than said adjacent surface portion of said filler material;
    irradiating diffuse radiation through said radiation permeable bottom foil and through said gap around said filler material with said radiation source so as to cast shadows of filled nests onto said receiving surface of said radiation receiver such that shadows of said nests inappropriately filled differ from shadows of said nests appropriately filled;
    generating a signal with said receiver upon casting thereon said shadows of said nests inappropriately filled; and
    triggering said sorting apparatus with said signal so as to sort out said inappropriately filled packages.

2. The process of claim 1 further comprising triggering said sorting apparatus only upon said signal failing to reach a predetermined threshold value.

3. The process of claim 2 wherein said signal comprises an electrical signal having a variable voltage and further using a voltage source for providing said predetermined threshold value such that said predetermined threshold value comprises a threshold voltage and wherein said triggering is effected only upon said variable voltage failing to reach said threshold voltage.

4. The process of claim 1 wherein said gap comprises a substantially annular gap and wherein said irradiating further comprises irradiating said diffuse radiation through said annular gap.

5. A process using a radiation source of diffuse radiation, a radiation receiver and a sorting apparatus for detecting and sorting out packages of filler material inappropriately filled during movement of said packages through a packaging machine wherein each of said packages comprises a cover foil and a radiation reflecting bottom foil having a plurality of nest formed therein for holding said filler material such that each of said nests is dimensioned to form a gap around said filler material after filling of said nests, and wherein said process comprises:
    disposing said source of radiation over said radiation receiver;
    providing said radiation receiver with an active receiving surface overlying an adjacent surface portion of said filler material such that said receiving surface is larger than said adjacent surface portion of said filler material;
    reflecting said diffuse radiation from said source of radiation from said radiation reflecting bottom foil through said gap around said filler material so as to cast shadows of filled nests onto said receiving surface of said radiation receiver such that shadows of said nests inappropriately filled differ from shadows of said nests appropriately filled;
    generating a signal with said receiver upon casting thereon said shadows of said nests inappropriately filled; and
    triggering said sorting apparatus with said signal so as to sort out said inappropriately filled packages.

6. The process of claim 5 further comprising triggering said sorting apparatus only upon said signal failing to reach a predetermined threshold value.

7. The process of claim 5 wherein said signal comprises an electrical signal having a variable voltage and further using a voltage source for providing said predetermined threshold value such that said predetermined threshold value comprises a threshold voltage and wherein said triggering is effected only upon said variable voltage failing to reach said threshold voltage.

8. The process of claim 5 wherein said gap comprises a substantially annular gap and wherein said irradiating further comprises irradiating said diffuse radiation through said annular gap.

9. A system for detecting and sorting out inappropriately filled packages of filler material filled during a packaging process, said system comprising:
    a cover foil provided on each of said packages;
    a radiation-permeable bottom foil provided on each of said packages and having a plurality of spaced nests formed in said bottom foil along at least one row for holding said filler material, said nests being dimensioned to form a gap around said filler material after filling of said nests;
    a radiation source for irradiating diffuse radiation through said radiation-permeable bottom foil after filling of said nests during said packaging process such that said radiation subsequently passes through said gap around said filler material;
    a radiation receiver provided for each said at least one row of said nests and having an active receiving surface overlying an adjacent surface portion of said filler material disposed in one of said nests, said active receiving surface of said radiation receiver being larger than said adjacent surface portion of said filler material such that said radiation passing through said gap casts a shadow of said one of said nests onto said active receiving surface of said radiation receiver wherein a shadow of said one of said nests inappropriately filled differs from a shadow of said one of said nests appropriately filled such that said receiver generates an output signal having an amplitude corresponding to each said shadow;

a comparator connected to each said radiation receiver;

a counter connected to each said comparator for counting said nests in said at least one row; and means connected to each said comparator and to each said counter for triggering a sorting mechanism upon said amplitude of said output signal being below a predetermined value.

10. A system for detecting and sorting out inappropriately filled packages of filler material filled during a packaging process, said system comprising;

a cover foil provided on each of said packages;

a radiation reflecting bottom foil having a plurality of nests formed therein along at least one row for holding said filler material such that each of said nests is dimensioned to form a gap around said filler material after filling of said nests;

a radiation source for irradiating diffuse radiation through said gap around said filler material and onto said radiation reflecting bottom foil after filling of said nests during said packaging process such that said radiation is reflected from said radiation reflecting bottom foil;

at least one radiation receiver disposed under said radiation source for measuring said radiation reflected from said radiation reflecting bottom foil and provided for each said at least one row of said nests and having an active receiving surface overlying an adjacent surface portion of said filler material disposed in one of said nests, said active receiving surface of said radiation receiver being larger than said adjacent surface portion of said filler material such that said radiation reflected from said radiation reflecting bottom foil passes through said gap around said filler material and casts a shadow of one of said nests onto said active receiving surface of said radiation receiver wherein a shadow of said one of said nests inappropriately filled differs from a shadow of said one of said nests appropriately filled such that said receiver generates an output signal having an amplitude corresponding to each said shadow;

a comparator connected to each said at least one radiation receiver;

a counter connected to each said comparator for counting said nests in said at least one row; and means connected to each said comparator and to each said counter for triggering a sorting mechanism upon said amplitude of said output signal being below a predetermined value.

11. A system for detecting and sorting out inappropriately filled packages of filler material filled during a packaging process, said system comprising:

a cover foil provided on each of said packages;

a radiation-permeable bottom foil provided on each of said packages and having a plurality of spaced nests formed in said bottom foil along at least one row for holding said filler material, said nests being dimensioned to form a gap around said filler material after filling of said nests;

a radiation source for irradiating diffuse radiation through said radiation-permeable bottom foil after filling of said nests during said packaging process such that said radiation subsequently passes through said gap around said filler material;

a radiation receiver provided for each said at least one row of said nests and having an active receiving surface overlying an adjacent surface portion of said filler material disposed in one of said nests, said active receiving surface of said radiation receiver being larger than said adjacent surface portion of said filler material such that said radiation passing through said gap casts a shadow of said one of said nests onto said active receiving surface of said radiation receiver wherein a shadow of said one of said nests inappropriately filled differs from a shadow of said one of said nests appropriately filled such that said receiver generates an output signal having an amplitude corresponding to each said shadow;

a comparator connected to each said radiation receiver; and means connected to each said comparator for triggering a sorting mechanism upon said amplitude of said output signal being below a predetermined value.

12. A system for detecting and sorting out inappropriately filled packages of filler material filled during a packaging process, said system comprising:

a cover foil provided on each of said packages;

a radiation reflecting bottom foil having a plurality of nests formed therein along at least one row for holding said filler material such that each of said nests is dimensioned to form a gap around said filler material after filling of said nests;

a radiation source for irradiating diffuse radiation through said gap around said filler material and onto said radiation reflecting bottom foil after filling of said nests during said packaging process such that said radiation is reflected from said radiation reflecting bottom foil;

at least one radiation receiver disposed under said radiation source for measuring said radiation reflected from said radiation reflecting bottom foil and provided for each said at least one row of said nests and having an active receiving surface overlying an adjacent surface portion of said filler material disposed in one of said nests, said active receiving surface of said radiation receiver being larger than said adjacent surface portion of said filler material such that said radiation reflected from said radiation reflecting bottom foil passes through said gap around said filler material and casts a shadow of one of said nests onto said active receiving surface of said radiation receiver wherein a shadow of said one of said nests inappropriately filled differs from a shadow of said one of said nests appropriately filled such that said receiver generates an output signal having an amplitude corresponding to each said shadow;

a comparator connected to each said at least one radiation receiver; and means connected to each said comparator for triggering a sorting mechanism upon said amplitude of said output signal being below a predetermined value.

* * * * *